(12) United States Patent
Taskin et al.

(10) Patent No.: US 11,648,393 B2
(45) Date of Patent: May 16, 2023

(54) IMPLANTABLE BLOOD PUMP WITH THROMBUS DIVERTER

(71) Applicant: HeartWare, Inc., Miami Lakes, FL (US)

(72) Inventors: Mustafa E. Taskin, Cooper City, FL (US); Charles R. Shambaugh, Coral Gables, FL (US)

(73) Assignee: HeartWare, Inc., Miami Lakes, FL (US)

( * ) Notice: Subject to any disclaimer, the term of this patent is extended or adjusted under 35 U.S.C. 154(b) by 128 days.

(21) Appl. No.: 17/144,290

(22) Filed: Jan. 8, 2021

(65) Prior Publication Data
US 2021/0290938 A1 Sep. 23, 2021

Related U.S. Application Data

(60) Provisional application No. 62/990,600, filed on Mar. 17, 2020.

(51) Int. Cl.
*A61M 60/226* (2021.01)
*A61M 60/857* (2021.01)
*A61M 60/165* (2021.01)

(52) U.S. Cl.
CPC ........ *A61M 60/857* (2021.01); *A61M 60/226* (2021.01); *A61M 60/165* (2021.01)

(58) Field of Classification Search
CPC .............. A61M 60/857; A61M 60/226; A61M 60/165; A61M 60/232; A61M 60/422; A61M 60/81; A61M 60/859; A61M 60/178
See application file for complete search history.

(56) References Cited

U.S. PATENT DOCUMENTS

| | | | |
|---|---|---|---|
| 6,688,861 B2 | 2/2004 | Wampler | |
| 7,575,423 B2 | 8/2009 | Wampler | |
| 7,976,271 B2 | 7/2011 | LaRose et al. | |
| 7,997,854 B2 | 8/2011 | LaRose et al. | |
| 8,152,493 B2 | 4/2012 | LaRose et al. | |
| 8,419,609 B2 | 4/2013 | Shambaugh, Jr. et al. | |
| 8,512,013 B2 | 8/2013 | LaRose et al. | |
| 10,279,093 B2 | 5/2019 | Reichenbach et al. | |
| 2011/0144413 A1* | 6/2011 | Foster | A61M 60/814 600/16 |
| 2015/0285258 A1* | 10/2015 | Foster | F04D 29/0467 415/203 |

(Continued)

FOREIGN PATENT DOCUMENTS

| | | |
|---|---|---|
| EP | 2461465 A1 | 6/2012 |
| EP | 2774633 A1 | 9/2014 |

(Continued)

OTHER PUBLICATIONS

PCT/US2021/017163, The International Search Report and Written Opinion, dated Apr. 19, 2021.

*Primary Examiner* — Ankit D Tejani
*Assistant Examiner* — Joshua Brendon Solomon
(74) *Attorney, Agent, or Firm* — Shumaker & Sieffert, P.A.

(57) ABSTRACT

An inflow cannula for an implantable blood pump having an impeller defining a plurality of flow channels, the inflow cannula includes a proximal end a distal end proximate the impeller, the distal end including a protuberance extending outward from the inflow cannula.

17 Claims, 5 Drawing Sheets

(56) References Cited

U.S. PATENT DOCUMENTS

| | | | |
|---|---|---|---|
| 2017/0143884 A1* | 5/2017 | Tanaka | F04D 29/4273 |
| 2017/0266358 A1* | 9/2017 | Aber | A61M 60/419 |
| 2019/0054221 A1 | 2/2019 | Casas | |
| 2019/0262518 A1* | 8/2019 | Molteni | A61M 60/818 |

FOREIGN PATENT DOCUMENTS

| | | |
|---|---|---|
| GB | 2527059 | 12/2015 |
| WO | 20140036060 A1 | 3/2014 |

* cited by examiner

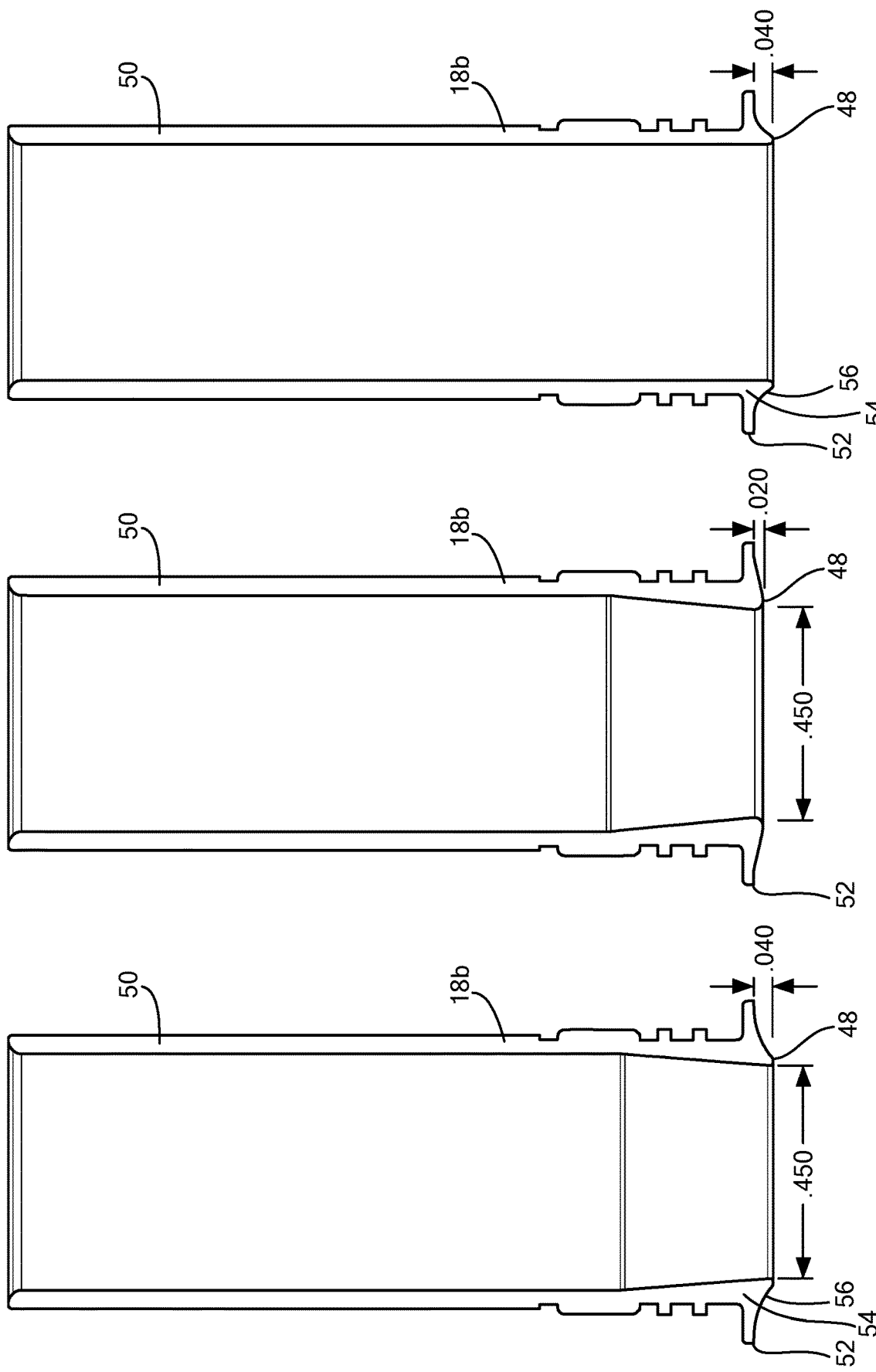

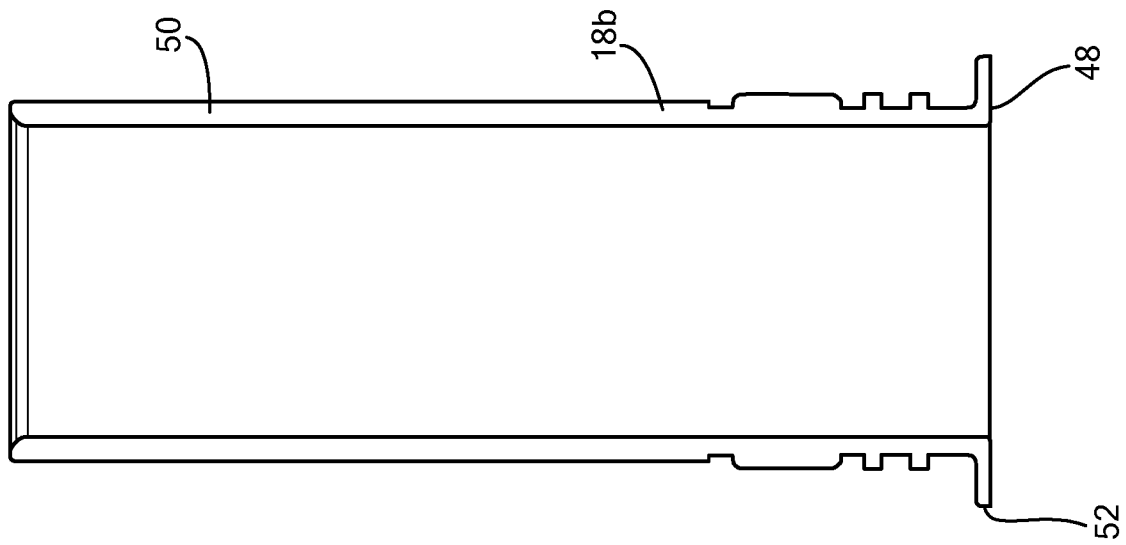
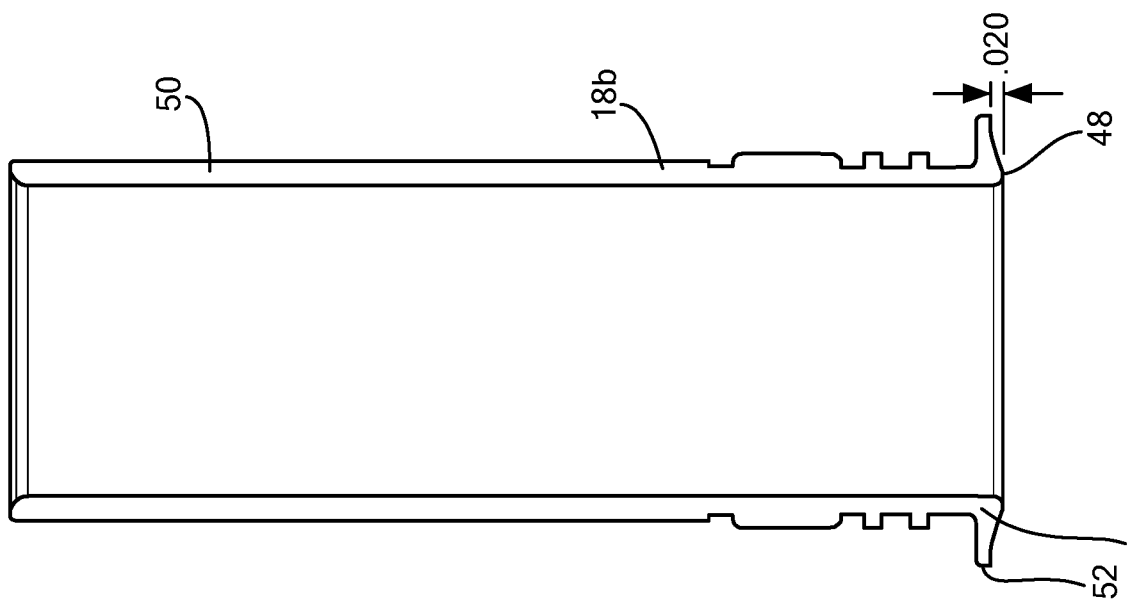

IMPLANTABLE BLOOD PUMP WITH THROMBUS DIVERTER

CROSS-REFERENCE TO RELATED APPLICATION

This application claims the benefit of U.S. Application Ser. No. 62/990,600, filed Mar. 17, 2020.

FIELD

The present technology is generally related to implantable blood pumps, and in particular, inflow cannulas.

BACKGROUND

Implantable blood pumps are commonly used to assist the pumping action of a failing heart and typically include a housing with an inlet, an outlet, and a rotor mounted therein. The inlet may be connected to a chamber of the patient's heart, typically the left ventricle, using an inflow cannula. The outlet may be connected to an artery, such as the aorta. Rotation of the rotor drives blood from the inlet towards the outlet and thus assists blood flow from the chamber of the heart into the artery. A known type of blood pump is a ventricular assist device ("VAD") with examples including, but not limited to, the HVAD® pump and the MVAD® pump manufactured by HeartWare, Inc. in Miami Lakes, Fla., USA.

A known adverse event associated with implanted blood pumps is the accumulation of thrombus on the rotor, which can lead to pump malfunctions or physiological effects. A common location for development of thrombus is on the thrust bearings of the rotor, which are adjacent to the shroud relief. Inner tubes 2 of inflow cannulas 4 of existing of blood pumps, as shown in FIG. 1, define right angles with a smooth transition between a first portion 6 and a substantially flat second portion 8 of the inner tube 2.

SUMMARY

The techniques of this disclosure generally relate to inflow cannulas for implantable blood pumps.

In one aspect, the present disclosure provides for an inflow cannula for an implantable blood pump having an impeller defining a plurality of flow channels, the inflow cannula includes a proximal end a distal end proximate the impeller, the distal end including a protuberance extending outward from the inflow cannula.

In another aspect of this embodiment, the inflow cannula includes a curved portion at the distal end, and wherein the protuberance is disposed on the curved portion.

In another aspect of this embodiment, the inflow cannula includes a first portion and a second portion orthogonal to the first portion, and wherein the curved portion is disposed between the first portion and the second portion.

In another aspect of this embodiment, the protuberance extends at an oblique angle from the curved portion.

In another aspect of this embodiment, the protuberance extends in a direction toward the impeller.

In another aspect of this embodiment, the inflow cannula includes an inner tube surrounded by an outer tube, and wherein the protuberance is disposed on the inner tube.

In another aspect of this embodiment, the protuberance is configured to divert thrombus particles toward the plurality of flow channels.

In another aspect of this embodiment, the protuberance is bulbous in shape.

In one aspect, an implantable blood pump includes an inflow cannula defining a proximal end and a distal end. An impeller is proximate the distal end. The impeller defines a plurality of flow channels. The inflow cannula defines a protuberance at its distal end, the protuberance being configured to divert thrombus particles toward the plurality of flow channels.

In another aspect of this embodiment, the inflow cannula includes a curved portion at the distal end, and wherein the protuberance is disposed on the curved portion.

In another aspect of this embodiment, the inflow cannula includes a first portion and a second portion orthogonal to the first portion, and wherein the curved portion is disposed between the first portion and the second portion.

In another aspect of this embodiment, the impeller defines a shroud relief, and wherein the protuberance extends toward the shroud relief.

In another aspect of this embodiment, the protuberance extends at an oblique angle from the curved portion.

In another aspect of this embodiment, the protuberance extends in a direction toward the impeller.

In another aspect of this embodiment, the inflow cannula includes an inner tube surrounded by an outer tube, and wherein the protuberance is disposed on the inner tube.

In another aspect of this embodiment. the protuberance is bulbous in shape.

In one aspect, an implantable blood pump includes an inflow cannula defining a proximal end and a distal end, the inflow cannula defining an inner tube and an outer tube. The inner tube defines a first portion, a second portion orthogonal to the first portion, and a curved portion, the curved portion being disposed at the distal end of the inner tube between the first portion and the second portion. An impeller is disposed proximate the distal end, the impeller defining a plurality of flow channels and a shroud relief. The inflow cannula defines a protuberance at its distal end extending from the curved portion at an oblique angle toward the shroud relief, the protuberance being configured to divert thrombus particles toward the plurality of flow channels.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 4A is a front cross-sectional of an exemplary inner tube of inflow cannula constructed in accordance with the principles of the present application;

FIG. 4B is a front cross-sectional of an exemplary inner tube of inflow cannula constructed in accordance with the principles of the present application;

FIG. 4C is a front cross-sectional of an exemplary inner tube of inflow cannula constructed in accordance with the principles of the present application;

FIG. 4D is a front cross-sectional of an exemplary inner tube of inflow cannula constructed in accordance with the principles of the present application; and FIG. 4E is a front cross-sectional of an exemplary inner tube of inflow cannula constructed in accordance with the principles of the present application.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Figure 1:
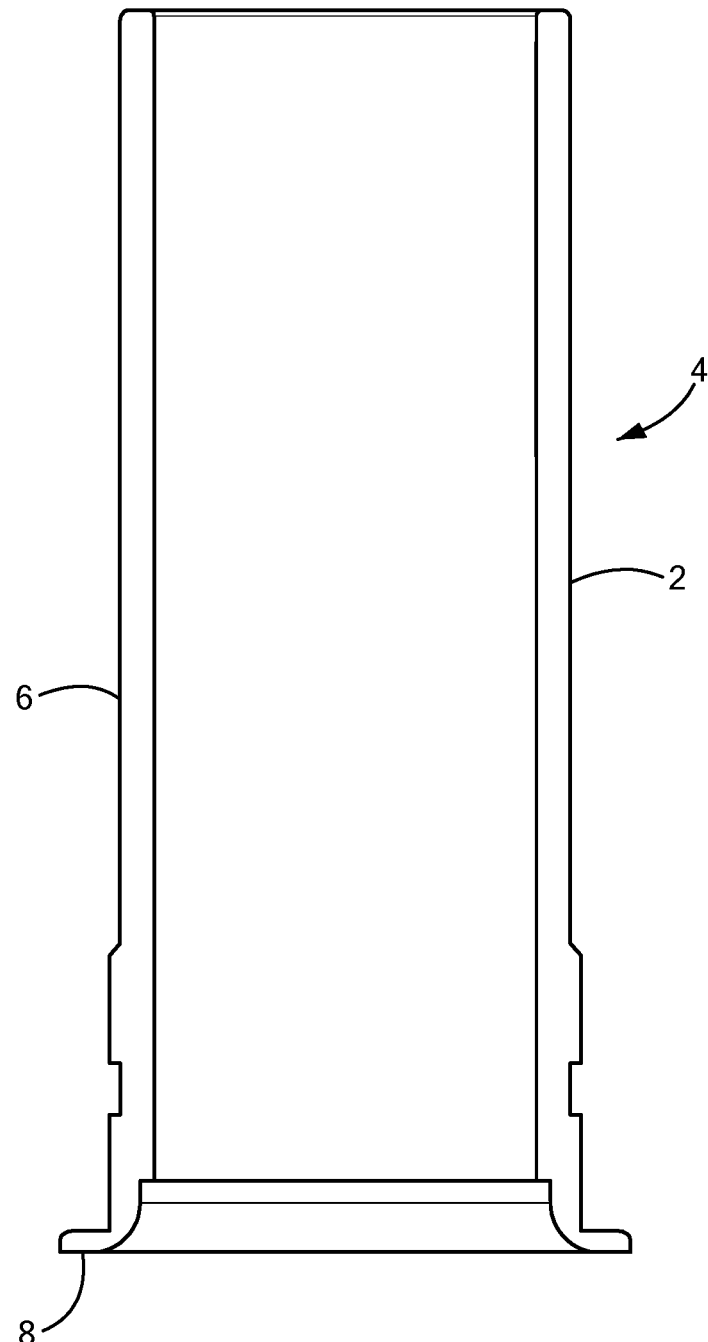
FIG. 1 is a front cross-sectional view of an inner tube of a prior art inflow cannula.
Figure 2:
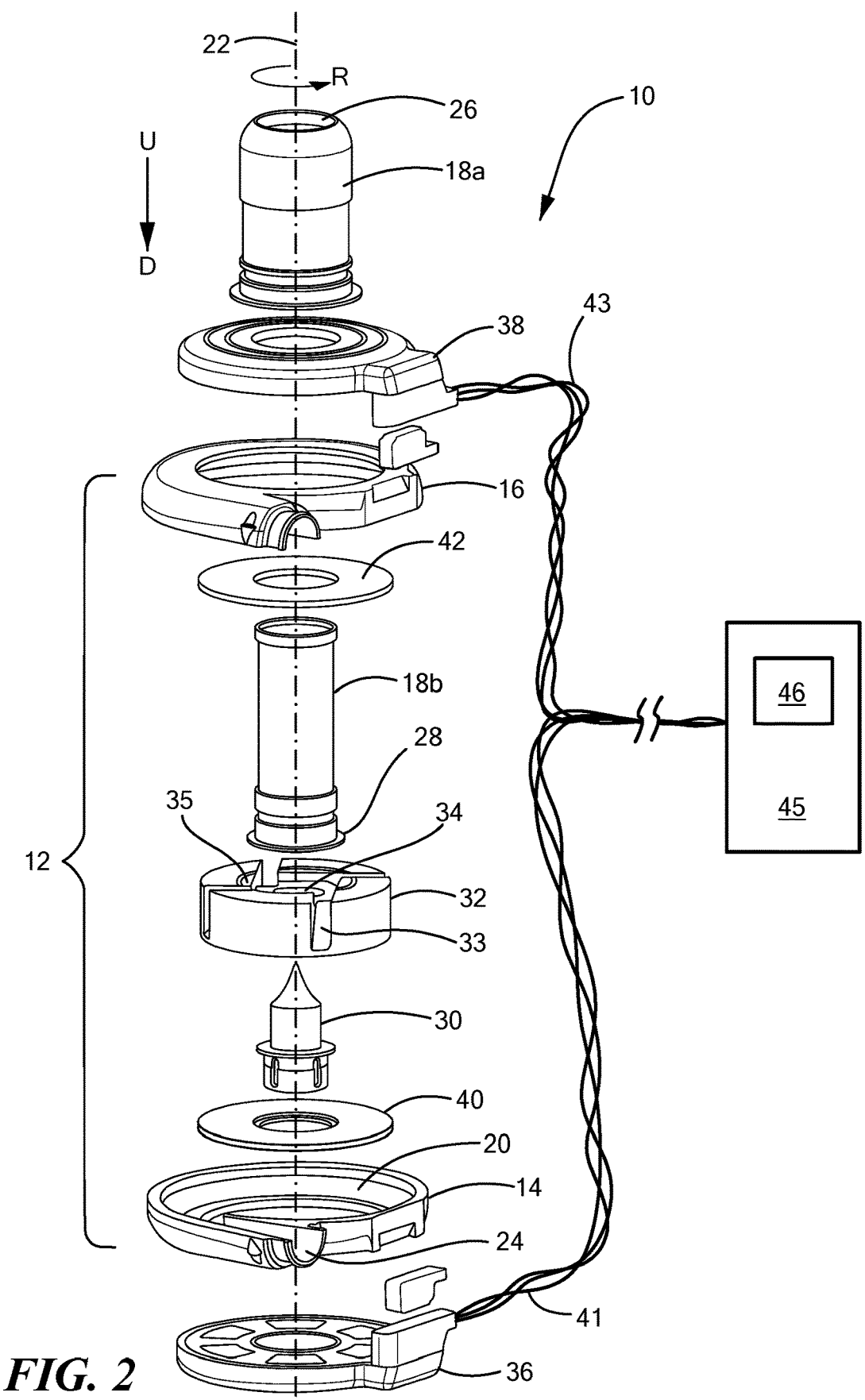
FIG. 2 is an exploded view of an exemplary blood pump constructed in accordance with the principles of the present application.

Referring now to the drawings in which like reference designators refer to like elements there is shown in FIG. 2 an exemplary blood pump constructed in accordance with the principles of the present application and designated generally "10." The blood pump 10 according to one embodiment of the disclosure includes a static structure or housing 12 which houses the components of the blood pump 10. In one configuration, the housing 12 includes a lower housing or first portion 14, an upper housing or second portion 16, and an inlet portion or inflow cannula 18 which includes an outer tube 18a and an inner tube 18b. The first portion 14 and the second portion 16 cooperatively define a volute-shaped chamber 20 having a major longitudinal axis 22 extending through the first portion and inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls.

Figure 3:
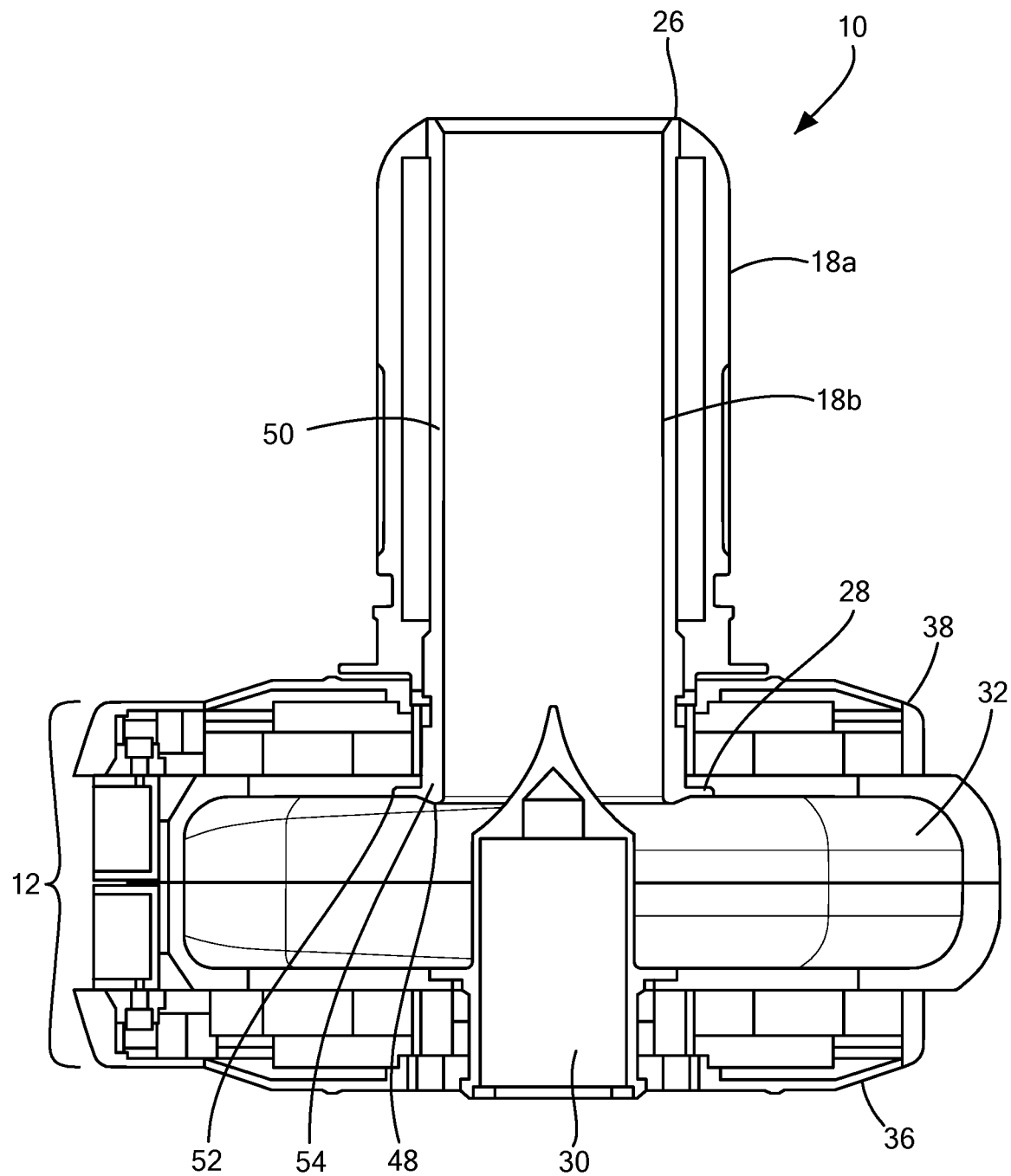
FIG. 3 is a cross-sectional view of the assembled blood pump shown in FIG. 2.

Referring now to FIGS. 2 and 3, the inflow cannula 18 is generally cylindrical and extends from first portion 14 and extends generally along axis 22. The inflow cannula 18 has an upstream end or proximal end 26 remote from second portion 16 and a downstream end or distal end 28 proximate the chamber 20. The parts of the housing 12 mentioned above are fixedly connected to one another so that the housing 12 as a whole defines a continuous enclosed flow path. The flow path extends from upstream end 26 at the upstream end of the flow path to the outlet 24 at the downstream end of the flow path. The upstream and downstream directions along the flow path are indicated in FIG. 2 by the arrows U and D respectively. A post 30 is mounted to first portion 14 along axis 22. A generally disc-shaped ferromagnetic rotor or impeller 32 with a central hole 34 is mounted within chamber 20 for rotation about the axis 22. Rotor 32 includes a permanent magnet and also includes flow channels 33 for transferring blood from adjacent the center of the rotor 32 to the periphery of the rotor 32. The rotor 32 further defines a shroud relief 35 configured to engage the distal end 28 of the inner tube 18b. In the assembled condition, post 30 is received in the central hole of the rotor 32. A first stator 36 having a plurality of coils may be disposed within the first portion 14 downstream from the rotor 32. The first stator 36 may be axially aligned with the rotor along axis 22 such that when a current is applied to the plurality of coils in the first stator 36, the electromagnetic forces generated by the first stator 36 rotate the rotor 32 and pump blood. A second stator 38 may be disposed within the second portion 16 upstream from the rotor 32. The second stator 38 may be configured to operate in conjunction with or independently of the first stator 36 to rotate the rotor 32.

Electrical connectors 41 and 43 (FIG. 2) are provided on the first stator 36 and the second stator 38 respectively for connecting the coils to a source of power such as a controller 45 having processing circuitry 46. The controller is arranged to apply power to the coils of the pump to create a rotating magnetic field which spins rotor 32 around axis 22 in a predetermined first direction of rotation, such as the direction R indicated by the arrow in FIG. 2, i.e., counterclockwise as seen from the upstream end of inflow cannula 18. In other configurations of the blood pump 10, the first direction may be clockwise. Rotation of the rotor 32 impel blood downstream along the flow path so that the blood, moves in a downstream direction D along the flow path, and exits through the outlet 24. During rotation, hydrodynamic and magnetic bearings (not shown) support the rotor 32 and maintain the rotor 32 out of contact with elements of the first portion 14 and the second portion 16 during operation. For example, the bearings maintain the rotor 32 out of contact from respective non-ferromagnetic discs 40 and 42. The general arrangement of the components described above may be similar to the blood pump 10 used in the MCSD sold under the designation HVAD by HeartWare, Inc., assignee of the present application. The arrangement of components such as the magnets, electromagnetic coils, and hydrodynamic bearings used in such a pump and variants of the same general design are described in U.S. Pat. Nos. 6,688,861; 7,575,423; 7,976,271; and 8,419,609, the disclosures of which are hereby incorporated by reference herein.

Referring now to FIGS. 3 and 4A-4E, the inner tube 18b may include a protuberance 48 at the distal end 28 of the inflow cannula 18. The protuberance 48 is configured to divert or otherwise direct particles in the blood, such as thrombus, toward the plurality of flow channels 33 on the impeller 32 and away from the shroud relief 35 thus preventing thrombus formation on the thrust bearings of the impeller. In one configuration, the protuberance 48 is bulbous in shape and extends outward from the inner tube 18b beneath the shroud relief 35 on the impeller 32. In an exemplary configuration, the inner tube 18b includes first portion 50 which extends parallel to the outer tube 18a and a second portion 52 then extends perpendicular to the first portion 38. Disposed between the first portion 50 and the second portion 52 is a curved portion 54. In one configuration shown in FIG. 3, the curved portion includes the protuberance 48 at the point of its maximum curvature.

In other configurations, as shown in FIGS. 4A-4E, the protuberance 48 may be disposed anywhere between the first portion 50 and the second portion 52. Additionally, the protuberance 48 may extend at an oblique angle. For example, as shown in FIG. 4A-4D, the protuberance 48 extends at approximately a 45-degree angle from the curved portion 54 to a position beneath the second portion 52 when the pump is assembled. In an exemplary configuration, the protuberance 48 extends between 0.02 and 0.04 inches away from the second portion 52 when the pump is assembled. In another configuration, the protuberance 48 extends in the same direction to that of the first portion 50. For example, as shown in FIGS. 4C-4E, the protuberance is substantially aligned with the first portion 50 and extends beneath the second portion 52. In some configurations, the protuberance defines a concavity 56 with the second portion 52, as shown in FIGS. 4A and 4C. The inner tube 18b may also taper in width as it extends distally from its proximal end. For example, as shown in FIGS. 4A-4B, the inner tube 18b tapers as it extends distally and includes the protuberance 48 at its distal end.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An implantable blood pump, comprising:
an inflow cannula defining a proximal end and a distal end, wherein the implantable blood pump defines a flow path from the proximal end to an outlet of a volute defined by a housing of the implantable blood pump, and wherein the distal end is downstream from the proximal end when the blood flows through the flow path; and
an impeller within the volute,
wherein the distal end is proximate the impeller,
wherein the impeller defines a shroud relief and a thrust bearing adjacent the shroud relief,
wherein the impeller includes a plurality of flow channels configured to transfer the blood flow from adjacent a center of the impeller to a periphery of the impeller, and
wherein the distal end defines a protuberance within the flow path, wherein the protuberance is configured to extend downstream of the shroud relief when the blood flows through the flow path to direct particles in the blood flow away from the shroud relief and the thrust bearing and toward the plurality of flow channels.

2. The implantable blood pump of claim 1, wherein the inflow cannula includes a curved portion at the distal end, and wherein the protuberance is disposed on the curved portion.

3. The implantable blood pump of claim 2, wherein the inflow cannula includes a first portion and a second portion orthogonal to the first portion, and wherein the curved portion is disposed between the first portion and the second portion, and wherein the protuberance is configured to extend downstream of the second portion when the blood flows through the flow path.

4. The implantable blood pump of claim 3, wherein the protuberance extends at an oblique angle from the curved portion.

5. The implantable blood pump of claim 2, wherein the inflow cannula includes an inner tube surrounded by an outer tube, and wherein the protuberance is disposed on the inner tube.

6. The implantable blood pump of claim 5, wherein the protuberance extends in a direction toward the impeller.

7. The implantable blood pump of claim 1, wherein the protuberance is bulbous in shape.

8. An implantable blood pump, comprising:
an inflow cannula including an inner tube surrounded by an outer tube and defining a proximal end and a distal end, wherein the implantable blood pump defines a flow path from the proximal end to an outlet of a volute defined by a housing of the implantable blood pump, and wherein the distal end is downstream from the proximal end when the blood flows through the flow path; and
an impeller within the volute and proximate the distal end,
wherein the impeller defines a shroud relief and a thrust bearing adjacent the shroud relief,
wherein the impeller defines a plurality of flow channels configured to transfer the blood flow from adjacent a center of the impeller to a periphery of the impeller,
wherein the inflow cannula defines a protuberance at the distal end, wherein the protuberance is disposed on the inner tube within the flow path, and
wherein the protuberance is configured to extend distally toward the impeller and downstream of the shroud relief when the blood flows through the flow path to divert thrombus particles in the blood flow away from the shroud relief and the thrust bearing and toward the plurality of flow channels.

9. The implantable blood pump of claim 8, wherein the inflow cannula includes a curved portion at the distal end, and wherein the protuberance is disposed on the curved portion.

10. The implantable blood pump of claim 9, wherein the inflow cannula includes a first portion and a second portion orthogonal to the first portion, and wherein the curved portion is disposed between the first portion and the second portion.

11. The implantable blood pump of claim 10, wherein the protuberance extends distally toward the shroud relief.

12. The implantable blood pump of claim 11, wherein the protuberance extends at an oblique angle from the curved portion.

13. The implantable blood pump of claim 8, wherein the protuberance is bulbous in shape.

14. An implantable blood pump, comprising:
an inflow cannula including an inner tube surrounded by an outer tube and defining a proximal end and a distal end, the inflow cannula defining an inner tube and an outer tube, the inner tube defining a first portion, a second portion orthogonal to the first portion, and a curved portion, the curved portion being disposed at the distal end of the inner tube between the first portion and the second portion, wherein the implantable blood pump defines a flow path from the proximal end to an outlet of a volute defined by a housing of the implantable blood pump, and wherein the distal end is downstream from the proximal end when the blood flows through the flow path; and
an impeller within the volute and proximate the distal end, the impeller defining a plurality of flow channels, a shroud relief, and a thrust bearing adjacent the shroud relief,
wherein the plurality of flow channels are configured to transfer the blood flow from adjacent a center of the impeller to a periphery of the impeller,
wherein the inflow cannula defines a bulbous protuberance at its distal end extending from the curved portion and disposed on the inner tube within the flow path,
wherein the curved portion defines a point of maximum curvature and the bulbous protuberance includes the point of maximum curvature, wherein the bulbous protuberance is configured to extend downstream of the second portion when the blood flows through the flow path, and wherein the bulbous protuberance is configured to extend downstream of the shroud relief when the blood flows through the flow path to divert thrombus particles in the blood flow away from the shroud relief and the thrust bearing and toward the plurality of flow channels.

15. The implantable blood pump of claim 6, wherein the curved portion defines a point of maximum curvature, and wherein the protuberance includes the point of maximum curvature.

16. The implantable blood pump of claim 5, wherein the inner tube tapers in width as the inner tube extends distally from the proximal end.

17. The implantable blood pump of claim 5, wherein the shroud relief is configured to engage a distal end of the inner tube.

* * * * *